US010466207B2

(12) United States Patent
Wang et al.

(10) Patent No.: US 10,466,207 B2
(45) Date of Patent: Nov. 5, 2019

(54) DISTRIBUTED FIBER SENSOR

(71) Applicant: The University of Massachusetts, Boston, MA (US)

(72) Inventors: Xingwei Wang, Shrewsbury, MA (US); Nan Wu, Sunderland, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 150 days.

(21) Appl. No.: 15/569,112

(22) PCT Filed: Apr. 29, 2016

(86) PCT No.: PCT/US2016/030074
§ 371 (c)(1),
(2) Date: Oct. 25, 2017

(87) PCT Pub. No.: WO2016/178981
PCT Pub. Date: Nov. 10, 2016

(65) Prior Publication Data
US 2018/0120267 A1  May 3, 2018

Related U.S. Application Data

(60) Provisional application No. 62/155,796, filed on May 1, 2015.

(51) Int. Cl.
*G01N 29/24* (2006.01)
*G01K 11/22* (2006.01)
*G01N 29/34* (2006.01)

(52) U.S. Cl.
CPC ......... *G01N 29/2462* (2013.01); *G01K 11/22* (2013.01); *G01N 29/2418* (2013.01); *G01N 29/34* (2013.01)

(58) Field of Classification Search
CPC ............... G01K 11/22; G01N 29/2418; G01N 29/2462; G01N 29/34
(Continued)

(56) References Cited

U.S. PATENT DOCUMENTS 6,783,494 B2 * 8/2004 Ogawa ................ A61B 5/0097
600/437
7,245,789 B2 * 7/2007 Bates ................... A61B 5/0097
359/285
(Continued)

FOREIGN PATENT DOCUMENTS

WO     2015051003 A1    4/2015

OTHER PUBLICATIONS

International Search Report for International Application No. PCT/US16/30074; International Filing Date: Apr. 29, 2016; dated Aug. 4, 2016; 9 pages.
(Continued)

*Primary Examiner* — Jacques M Saint Surin
(74) *Attorney, Agent, or Firm* — Cantor Colburn LLP

(57) ABSTRACT

In an embodiment, a sensor comprises a waveguide comprising a photoacoustic generation element disposed on the waveguide, the photoacoustic generation element comprising a photoabsorptive material; and a sensing element comprising an optical acoustic wave detector. In another embodiment, a sensing system comprises the sensor and a laser. In yet another embodiment, a method of sensing comprises providing the sensing system; heating the photoabsorptive material with a laser to generate an acoustic signal; sensing an intensity of laser light reflected by the optical acoustic wave detector to detect the acoustic signal; and determining a time of flight of the acoustic signal between the generation and the detection to determine a change in a parameter change in a medium between the photoabsorptive material and the optical acoustic wave detector.

20 Claims, 6 Drawing Sheets

(58) Field of Classification Search
USPC .......................................................... 73/649
See application file for complete search history.

(56) References Cited

U.S. PATENT DOCUMENTS

| | | | | |
|---|---|---|---|---|
| 2013/0160557 | A1* | 6/2013 | Nakajima | G01H 9/00 |
| | | | | 73/655 |
| 2013/0319123 | A1 | 12/2013 | Wang et al. | |
| 2015/0297092 | A1* | 10/2015 | Irisawa | A61B 5/0095 |
| | | | | 600/407 |
| 2016/0242653 | A1* | 8/2016 | Rourke | A61B 5/0097 |
| 2018/0110417 | A1* | 4/2018 | Wang | A61B 5/6852 |

OTHER PUBLICATIONS

Lou et al., "Deduction of the two-dimensional distribution of temperature in a cross section of a boiler furnace from images of flame radiation," Science Direct Combustion and Flame, pp. 97-105, vol. 143, 2005.

Pramanik et al., "Thermoacoustic and photoacoustic sensing of temperature"; Journal of Biomedical Optics, pp. 0540241-05402417, vol. 14(S), Sep./Oct. 2009.

Written Opinion of the International Search Report for International Application No. PCT/US16/30074; International Filing Date: Apr. 29, 2016; dated Aug. 4, 2016; 4 pages.

Yin et al., "Investigation of th Flow, Combustion, Heat-transfer and Emissions from a 609 MW Utility Tangentially Fired Pulverized-Coal Boiler," Fuel 81, pp. 997-1006, 2002.

Zhou et al., "Experimental investigations on visualization of three-dimensional temperature distributions in a large-scale pulverized-coal-fired boiler furnace," Science Direct Proceedings of the Combustion Inst., pp. 1699-1706, vol. 30, 2005.

Zhou et al., "Visualization of three-dimensional temperature distributions in a large-scale furnace via regularized reconstruction from radiative energy images: numerical studies"; J. of Quant. Spectroscopy & Radiative Transfer, pp. 361-383, vol. 72, 2002.

* cited by examiner

DISTRIBUTED FIBER SENSOR

CROSS REFERENCE TO RELATED APPLICATIONS

This application is a National Stage application of PCT/US2016/030074, filed Apr. 29, 2016, which claims the benefit of U.S. Provisional Application No. 62/155,796, filed May 1, 2015, both of which are incorporated by reference in their entirety herein.

GOVERNMENT LICENSE RIGHTS

This disclosure was made with government support under Grant No. DE-FE0023031 awarded by the Department of Energy. The government has certain rights in the disclosure.

BACKGROUND

Remote or noncontact sensing is desirable in applications where the environment to be sensed is incompatible with a sensing element. For example, in combustion processes, the temperature of the process may be greater than the sensing element can sustain. In such situations a remote or noncontact temperature sensor is desirable because the temperature sensor can be physically separated from the process. Furthermore, in some applications, development of a temperature distribution is desirable. In such applications, such as boiler monitoring, fuel cell monitoring, and a variety of manufacturing processes, an array of sensors that can provide two-dimensional or three-dimensional temperature information is desired. Currently available techniques use indirect approaches to estimate temperature distribution. For example, temperature distributions may be estimated using infrared imaging and numerical modeling. Nonetheless there remains a need for an improved noncontact sensor which can provide temperature information.

SUMMARY

Disclosed is a sensor including: a waveguide including a photoacoustic generation element disposed on the waveguide, the photoacoustic generation element including a photoabsorptive material; and a sensing element including an optical acoustic wave detector.

Also disclosed is a sensing system comprising the sensor and a laser.

Also disclosed is a method of sensing comprises providing the sensing system; heating the photoabsorptive material with a laser to generate an acoustic signal; sensing an intensity of laser light reflected by the optical acoustic wave detector to detect the acoustic signal; and determining a time of flight of the acoustic signal between the generation and the detection to determine a change in a parameter change in a medium between the photoabsorptive material and the optical acoustic wave detector.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Disclosed is a sensor which can measure temperature using an acoustic method, and a sensor system comprising the sensor, wherein the sensor system can provide two-dimensional or three-dimensional temperature distribution. Because temperature is determined acoustically and without direct contact, the sensor is applicable to high temperature applications. Also, use of the sensor in combination with optical fibers provides for a compact system adaptable to miniaturization and adaptable to distributed sensing to provide two-dimensional or three-dimensional information. In addition, as is further discussed below, the sensor is applicable to other applications, such as corrosion monitoring or monitoring materials for fracture.

Temperature can be determined acoustically based on the speed of sound propagating within a measured object. Temperature is governed by the formula $T=(c/b)^2$, wherein c is the speed of sound and B is the acoustic constant of air. Sound velocity may be determined by the time of flight of an acoustic wave divided by the flight distance. In the disclosed system, a photoabsorptive material is used to convert optical energy into acoustic energy, thereby generating an acoustic wave. A sensing element, such as a Bragg grating, can be used to detect the acoustic wave. Thus the time for an acoustic wave to transport from the photoabsorptive material to the sensing element and the distance the acoustic wave travels provides the average temperature over the path of the acoustic wave.

Figure 1:
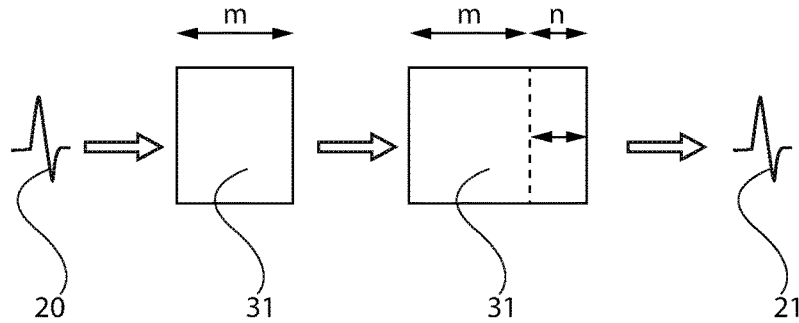
FIG. 1 is a schematic representation of an embodiment of a method of generating an acoustic pulse.

The generation of the acoustic wave is shown schematically in FIG. 1. For example, an optical wave 20 from a laser may be used to excite the photoabsorptive material in the photoacoustic generation element 31 having an initial length m. The photoacoustic generation element 31 is heated, causing expansion and contraction by a length n, thereby generating an acoustic signal 21.

Figure 2A:
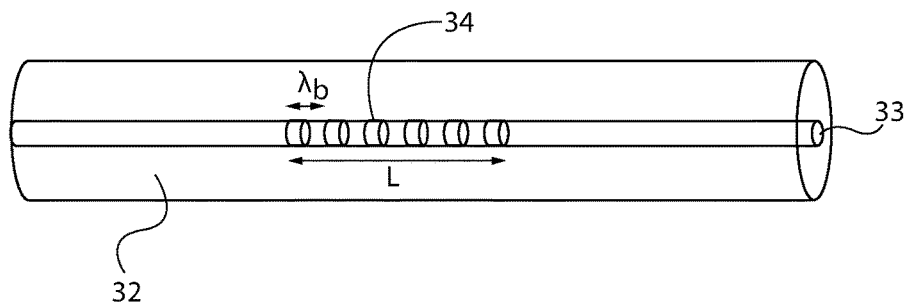
FIG. 2a is a schematic representation of an embodiment of a sensing element and a method of sensing.
Figures 2B, 2C:
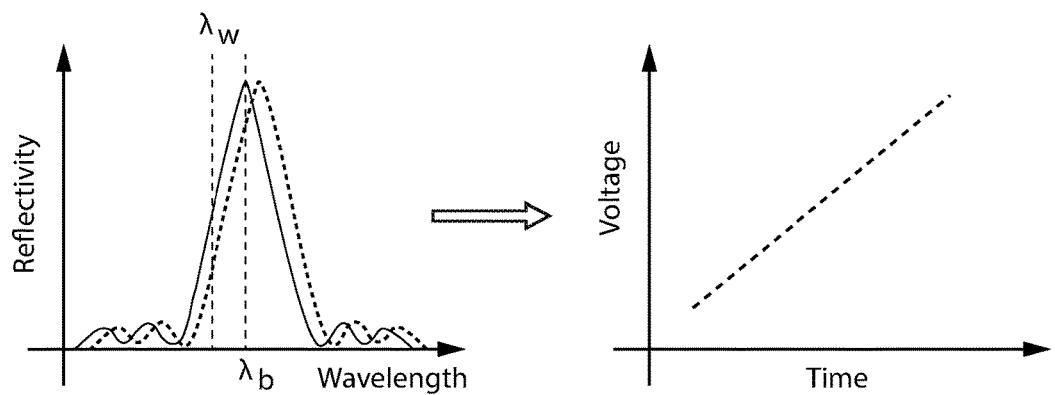
FIG. 2b is a graphical representation of an embodiment of a spectrum shift.
FIG. 2c is a graphical representation of an embodiment of a of a change in voltage output that can occur as the spectrum shifts with time.

The acoustic signal, for example, an acoustic wave may be detected using a Bragg grating, e.g., a fiber Bragg grating, embedded in an optical fiber 32 as shown in FIG. 2a. The Bragg grating 34 having a length L operates as an optical filter which selectively reflects signals having a Bragg wavelength $\lambda_b$. When the acoustic wave contacts the Bragg grating, the acoustic wave causes mechanical expansion or contraction, resulting in a change in the grating period and a change in the effect of refractive index of the grating, thereby shifting the Bragg wavelength. When interrogated by a laser, the shift in the Bragg wavelength can be observed as a change in reflectivity or the intensity of reflected light. FIG. 2b is a graphical representation of the spectrum shift that occurs as the Bragg grating senses the acoustic signal, where $\lambda_w$ is the working wavelength. FIG. 2c is a graphical representation of a change in voltage output that can occur as the spectrum shifts with time.

Disclosed is a sensor comprising: a waveguide comprising a photoacoustic generation element disposed on the waveguide, the photoacoustic generation element comprising a photoabsorptive material; and an optical fiber comprising a sensing element comprising an optical acoustic wave detector.

Also disclosed is a sensor comprising: a waveguide comprising a photoacoustic generation element disposed on the waveguide, the photoacoustic generation element comprising a photoabsorptive material, and a sensing element comprising an optical acoustic wave detector which is disposed in the waveguide.

Also disclosed is a sensor comprising: a waveguide comprising a photoacoustic generation element disposed on the waveguide, the photoacoustic generation element comprising a photoabsorptive material and an optical switch; and an optical fiber comprising a sensing element including an optical acoustic wave detector.

Also disclosed is a sensor comprising: a waveguide comprising a photoacoustic generation element disposed on the waveguide, the photoacoustic generation element comprising a photoabsorptive material and an optical switch; and a sensing element comprising an optical acoustic wave detector which is disposed in the waveguide.

The waveguide may comprise any suitable material which conducts light. Representative waveguides include transparent polymeric materials, such as acrylic, internally reflective tubes, glass, and optical fibers. An embodiment in which the waveguide is an optical fiber is specifically mentioned. The optical fiber may be a multimode fiber or a single mode fiber. In certain applications, use of a single mode fiber is preferred. Representative single mode fibers have a core diameter of 1 micrometer (μm) to 9 μm, 2 μm to 8 μm, or 3 μm to 7 μm.

In an embodiment, the waveguide may be an optical fiber, and the optical fiber of the waveguide may be a same optical fiber as the optical fiber of the sensing element. In another embodiment the waveguide and the optical fiber of the sensing element may be distinct, and thus the waveguide may be a first optical fiber and the sensing element may be disposed on a second optical fiber.

A photoacoustic generation element is disposed on the waveguide. The photoacoustic generation element comprises a photoabsorptive material. The photoabsorptive material may comprise gold, aluminum, silver, platinum, copper, carbon black, graphite, graphene, carbon nanotubes, a fullerene, or a combination thereof. The photoabsorptive material may comprise gold, carbon black, or a combination thereof. Also, the photoabsorptive material may be in the form of spheres, particles, rods, tubes, or a combination thereof, such as nanoparticles, nanorods, nanotubes, or a combination thereof. In an embodiment, the photoabsorptive material comprises gold nanoparticles, gold nanorods, gold coated carbon nanotubes, gold coated fullerene, or combination thereof. Use of gold nanoparticles is specifically mentioned.

The photoabsorptive material may have a particle size, e.g. a particle size as measured by light scattering, of 10 nanometers (nm) to 500 nm, 20 nm to 400 nm, or 40 nm to 300 nm. Also, it may be desirable to use a photoabsorptive material having a relatively narrow particle size distribution. Although not wanting to be bound by theory, it is understood that the particle size determines the absorption wavelength of the nanoparticles, and thus by using materials having a relatively narrow particle size distribution, a photoabsorptive material having a relatively narrow absorption band may be provided. Because the photoabsorptive of material has a relatively narrow absorption band, it is possible to select a photoacoustic generation element based on the wavelength of an excitation light. In an embodiment, at least 90% of the photoabsorptive material has a particle size within 10% of the average particle size of the photoabsorptive material. In another embodiment, at least 93% of the photoabsorptive material has a particle size within 10% of the average particle size of the photoabsorptive material. In yet another embodiment, at least 96% of the photoabsorptive material has a particle size within 10% of the average particle size of the photoabsorptive material. Also, 3 standard deviations of a particle size of the photoabsorptive material may be 1 nanometer to 50 nanometers, 2 nanometers to 40 nanometers, or 4 nanometers to 30 nanometers.

The photoabsorptive material can be embedded in a polymer matrix in the photoacoustic generation element. The polymer matrix can comprise a thermoset polymer. The polymer matrix can comprise a silicone polymer (such as polydimethylsiloxane), an epoxy, a polyester, a polyurethane, a formaldehyde resin, a polyimide, or a combination thereof. The polymer matrix can comprise a silicone polymer (such as polydimethylsiloxane), an epoxy, or a combination thereof The amount of photoabsorptive material in the photoacoustic generation element is not particularly limited, for example, the photoabsorptive material can be present in an amount of 5 to 50 wt %, or 10 to 30 wt %.

The length and thickness of the photoacoustic generation element can vary dependent upon the application. In an embodiment, the photoacoustic generation element can have a length of 0.1 to 50 mm, 0.5 to 30 mm, 1 to 20 mm, or 2 to 10 mm. In an embodiment, the photoacoustic generation element can have a thickness of 5 to 1,000 micrometers, 10 to 600 micrometers, 30 to 500 micrometers, or 50 to 250 micrometers. When a plurality of photoacoustic generation elements are present, the length of the each photoacoustic generation elements independently can be 0.1 to 10 mm, 0.5 to 5 mm, 1 to 2 mm.

A plurality of photoacoustic generation elements may be disposed on the waveguide. In an embodiment, the sensor comprises 1 to 3,000 photoacoustic generation elements, 2 to 2,500 photoacoustic generation elements, 4 to 2,000 photoacoustic generation elements, 6 to 1,500 photoacoustic generation elements, 8 to 1,000 photoacoustic generation elements, or 10 to 500 photoacoustic generation elements. The photoacoustic generation elements may be disposed on a single waveguide, e.g. a single optical fiber, or may be disposed on a plurality of optical fibers.

If desired the waveguide may comprise an etched portion. Etching improves scattering of light. By etching the waveguide, an intensity of laser light directed to the photoabsorptive material is increased, which can increase in intensity of an acoustic wave generated by the photoabsorptive material.

The sensing element comprises an optical acoustic wave detector. The optical acoustic wave detector may be a Bragg grating, such as a fiber Bragg grating. The sensor may comprise 1 to 3,000, 2 to 2,500, or 4 to 2,000 sensing elements.

Figure 3:
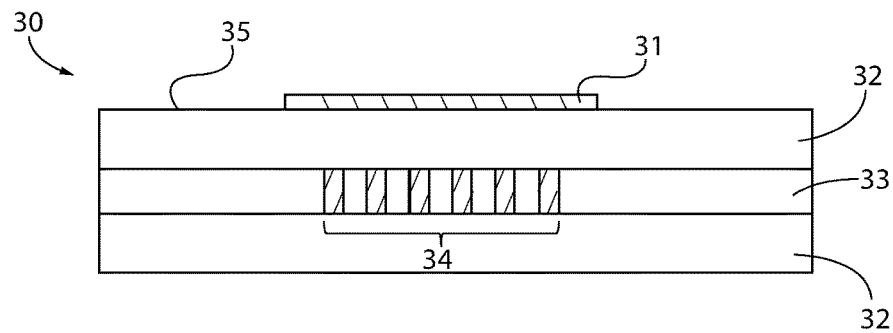
FIG. 3 is a schematic representation of an embodiment of a sensor.

An embodiment of the sensor is shown in FIG. 3. The sensor 30 comprises a photoacoustic generation element 31 disposed on a waveguide, e.g., on an outer surface 35 of an optical fiber. The optical fiber 32 may have a core 33, and a sensing element, e.g., a Bragg grating 34, may be disposed in the core. In another embodiment, the photoacoustic generation element may be disposed on a first optical fiber, and the sensing element may be disposed in a second optical fiber.

As noted above, use of a photoabsorptive material having a relatively narrow absorption band permits selection of a photoacoustic generation element based on the wavelength of the excitation light. Alternatively, an optical switch may be used to select a photoacoustic generation element. In an embodiment, the sensor comprises an optical switch, which may be used to selectively direct excitation light to a photoabsorptive material of a selected photoacoustic generation element. The photoacoustic generation element comprising the optical switch and the sensing element may be disposed on distinct waveguides. For example, in an embodiment, a waveguide comprising a photoacoustic generation element which comprises an optical switch may be disposed on a first optical fiber, and a sensing element comprising an optical acoustic wave detector, e.g. a fiber Bragg grating, may be disposed on a second optical fiber. Alternatively, the waveguide may comprise the photoacoustic generation element, which comprises the optical switch, and waveguide may also comprise the sensing element comprising the optical acoustic wave detector.

As shown in FIG. 3, each photoacoustic generation element 31 may be disposed adjacent a corresponding sensing element such as Bragg grating 34. Alternatively, the photoacoustic generation elements and the sensing elements may be disposed nonadjacent. A distance between adjacent sensing elements may be each independently selected to be 0.01 meter (m) to 1 m, 0.05 m to 0.8 m, or 0.1 m to 0.6 m. Also, an average distance between adjacent sensing elements may be 0.01 m to 1 m, 0.05 m to 0.8 m, or 0.1 m to 0.6 m.

A sensing system comprises the sensor and a laser. A first laser may be used to excite the photoabsorptive of material of the photoacoustic generation element, and a second laser may be used to interrogate the optical acoustic wave detector of the sensing element. Any suitable laser may be used. In an embodiment, the excitation laser has a wavelength of 500 nm to 550 nm, and the interrogation laser has a wavelength of 1520 nm to 1560 nm. As is further discussed above, the wavelength of the excitation laser is selected based on the absorption wavelength of the photoabsorptive material, and the wavelength of the interrogation laser is selected based on the wavelength of the optical acoustic wave detector.

Figure 4:
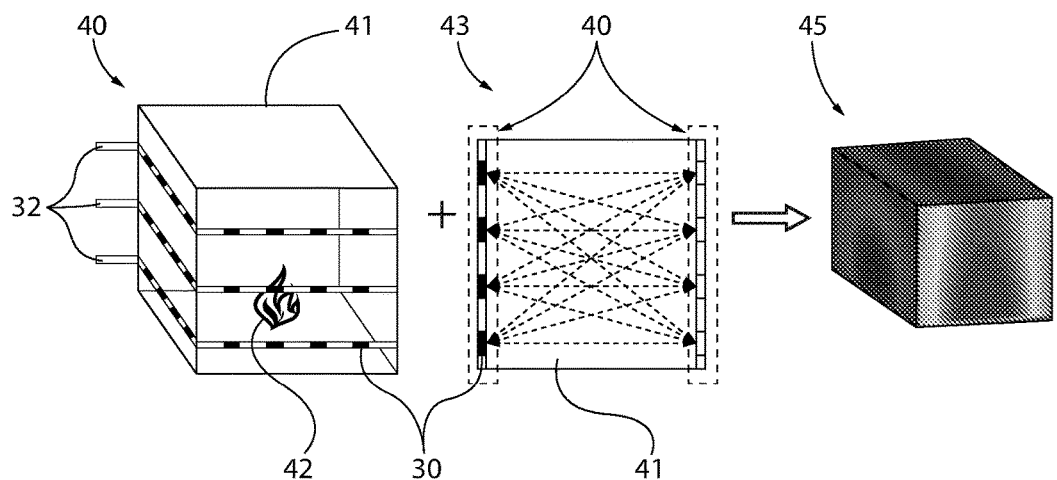
FIG. 4 is a schematic representation of an embodiment of a distributed sensing system and a reconstructed temperature distribution.

To provide two-dimensional or three-dimensional information, a distributed sensing system 40 may be provided, as illustrated schematically in FIG. 4. FIG. 4 illustrates a distributed sensing system 40 positioned to sense the temperature distribution around a heat source 42 in a boiler 41. The distributed sensing system 40 comprises a plurality of sensors 30, each disposed on an optical fiber 32. As is further discussed below, using a reconstruction algorithm 43 a two-dimensional or three-dimensional distribution such as three-dimensional distribution 45 may be developed. For example, when the sensor is a temperature sensor, use of the reconstruction algorithm provides a reconstructed temperature distribution, as shown in FIG. 4.

The distribution profile can be reconstructed using a recursive least-squares algorithm. Spatial discretization using Gaussian radial basis functions may be used. As noted above, the speed of acoustic waves depends on the temperature of the medium, and therefore a time-of-flight (TOF) of acoustic signal over a path may be calculated as:

$$TOF(l_j) = \int \frac{1}{C(x,y,z)} dl_j = \int \frac{1}{Z\sqrt{T(x,y,z)}} dl_j$$

wherein C(x,y,z) is the velocity of sound at position (x,y,z), Z is the ratio between the specific heats at constant pressure and the volume of the gas, and d(x,y,z) is the reciprocal of the sound velocity. Measurements of TOF provide information about the Interpol fax of temperature along the path between a photoacoustic generation element and a sensing element. The algorithm can provide d(x,y,z) from $1_j$, wherein j is an integer from 1 to M, wherein M is the number of paths a full cycle measurement. Once d(x,y,z) is available, a temperature distribution T(x,y,z) can be obtained using a deterministic algebraic relationship. Reconstruction of the temperature distribution may be obtained using a direct space discretization or a Fourier regularization algorithm. The direct space discretization or the Fourier regularization algorithm may be applied to a two-dimensional temperature distribution.

When using discrete space discretization, the space may be divided into N regions and d(x,y,z) in each individual region assigned to be uniformly $\bar{\omega}_i$. Hence, the entire distribution may be discretized represented by N unknown parameters. The TOF may be represented as $$TOF(l_j) = \sum_{i=1}^{N} \omega_i a_{ji}$$

wherein $a_{ji}$ is the length of the $j_{th}$ path inside the region. A set of N linear equations with N unknowns is established if there exist N different paths by solving these equations, $\bar{\omega}_i$ can be obtained. In an embodiment wherein M is not equal to N, unknown parameters can be found by minimizing a quadratic cost function of total output errors. Alternatively, Fourier parameterization may be used. For example, if a rectangular region has the dimensions $L_x$ and $L_y$, and d(x,y) is symmetric with respect to the x and y axes, and furthermore periodic with periods $2L_x$ and $2L_y$ in X-Y directions respectively, and a double Fourier series using only cosinusoidal terms may be provided. Omitting approximation errors, the TOF may be represented as $$TOF(l_k) = \sum_{i=0}^{\infty} \sum_{j=0}^{\infty} \omega_{ij} h_{k,ij} + n_k$$

wherein k is an integer from 1 to M, $$h_{k,ij} = \int \cos(i\pi u)\cos(j\pi v) dl_k, \text{ and } u = \frac{x}{L_k}; v = \frac{y}{L_y}.$$

The discretization algorithm disclosed above applies here as well to identify the linear parameters $\bar{\omega}_{ij}$.

Gaussian radial basis functions may also be used. The Gaussian radial basis function takes the form of $$\phi_i(X) = e^{\frac{\|X-X_i\|^2}{2\sigma_j^2}},$$

wherein $X_i$ and $\sigma_j$ are the predefined center invariance, and X is position with 3 dimensions, (x,y,z). Because any continuous nonlinear function over a compact set can be approximated by the summation of basis functions with the appropriate weights, $$f(X) \approx \sum_{i=1}^{N} \omega_i \phi_i(X)$$

TOF can be provided from $$TOF(l_j) = \int f(X) dl_j = \sum_{i=1}^{N} \left( \omega_i \int e^{\frac{\|X-X_i\|^2}{2\sigma_j^2}} dl_j \right)$$

to provide a set of linear equations with unknown similar to other approaches. While not want to be bound by theory, it is believed that use of Gaussian radial basis functions provides a better approximation that alternative methods. Also, a recursive least-squares algorithm can be used to estimate unknown parameters.

As a result, the disclosed sensor and sensor system can provide real-time continuous temperature distribution, providing enhanced monitoring methodologies.

In an embodiment, the sensing system is a temperature sensing system. Alternatively, a system for monitoring materials may be provided. For example, the acoustic properties of materials change if corrosion or fractures occur. The disclosed sensor can detect corrosion or fractures based on changes in the propagation of acoustic waves. Thus the disclosed sensor may be used to provide a corrosion sensor.

Also disclosed is a method of temperature sensing, the method comprising: providing the sensing system; heating the photoabsorptive material with a laser to generate an acoustic signal; sensing an intensity of laser light reflected by the optical acoustic wave detector to detect the acoustic signal; determining a time of flight of the acoustic signal between the generation and the detection to determine a temperature of a medium between the photoabsorptive material and the optical acoustic wave detector. In an embodiment, the laser may be directed into the waveguide, e.g., an optical fiber, to direct light onto the photo absorptive material. Also, the optical acoustic wave detector, e.g. a Bragg grating, may be interrogated using a laser having a wavelength corresponding to a Bragg wavelength of the optical acoustic wave detector. The heating may comprises selectively heating the photoabsorptive material of a selected photoacoustic generation element by contacting the photoabsorptive material of the selected photoacoustic generation element with laser light having a wavelength corresponding to an absorption wavelength of the photoabsorptive material of the selected photoacoustic generation element. Alternatively, the heating may comprise selectively heating the photoabsorptive material of a selected photoacoustic generation element by selecting the selected photoacoustic generation element with the optical switch.

The following non-limiting examples further illustrate the various embodiments described herein.

EXAMPLES

Figure 5A:
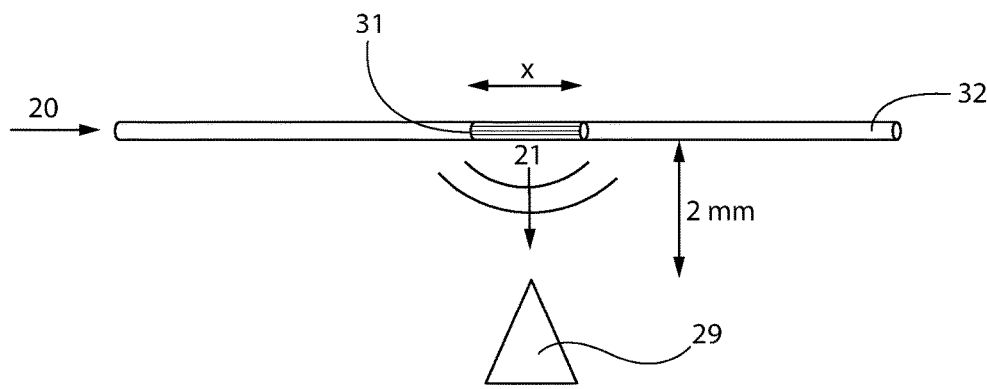
FIG. 5a is a schematic illustration of the experimental setup of Examples 1 and 2.

Examples 1-2: Effect of Length of the Photoacoustic Generation Element on the Acoustic Voltage Two photoacoustic generation elements were coated on an optical fiber. The photoacoustic generation elements comprised a gold nanocomposite that was prepared by blending a gold salt ($HAuCl_4 \cdot 3H_2O$) and carbon black in polydimethylsiloxane. As is illustrated in FIG. 5a, each photoacoustic generation element 31 was coated on a sidewall of a multimode optical fiber 32 with a core having a diameter of 400 micrometer and a cladding having a diameter of 425 micrometer. The photoacoustic generation element of Example 1 had a length, x, of 10 mm and the photoacoustic generation element of Example 2 had a length, x, of 2.5 mm. A power of 25 microjoules from the laser was excited on a fiber end and an acoustic sensing element 29 was located 2 millimeters away from the photoacoustic generation element.

Figure 5B:
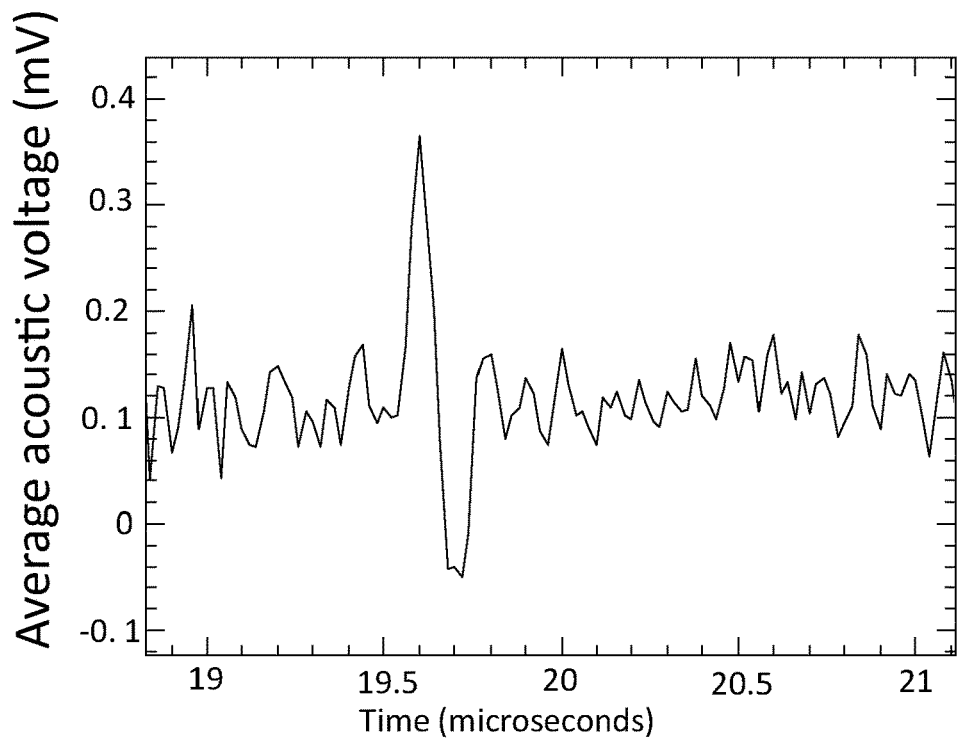
FIGS. 5b and 5c are graphical illustrations of the average acoustic voltages of Examples 1 and 2.
Figure 5C:
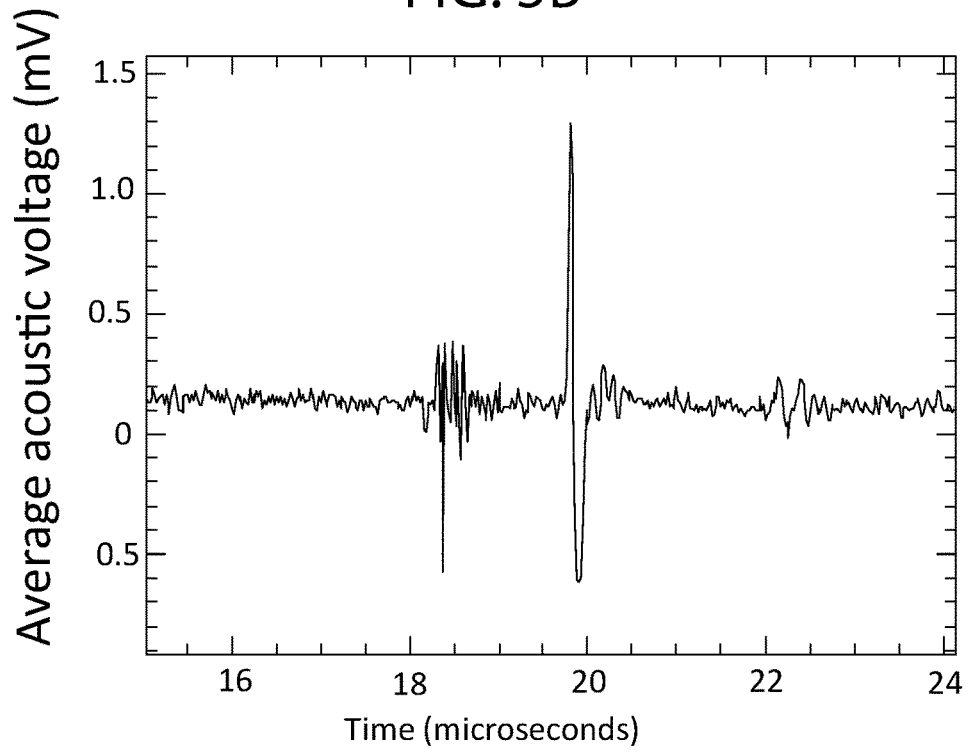

The average acoustic voltages with time are shown in FIG. 5b ad FIG. 5c for Examples 1 and 2, respectively. FIG. 5b ad FIG. 5c illustrate that a peak average acoustic value of the photoacoustic generation element of about 1.3 mV of Example 2 is almost 3 times that of about 0.4 mV of Example 1. The acoustic pressure was then determined based on the voltages in FIG. 5b and FIG. 5c to be 8 kilopascals and 29 kilopascals, respectively.

Examples 3-4: Corrosion Detection Using a Photoacoustic Generation Element

Figure 6:
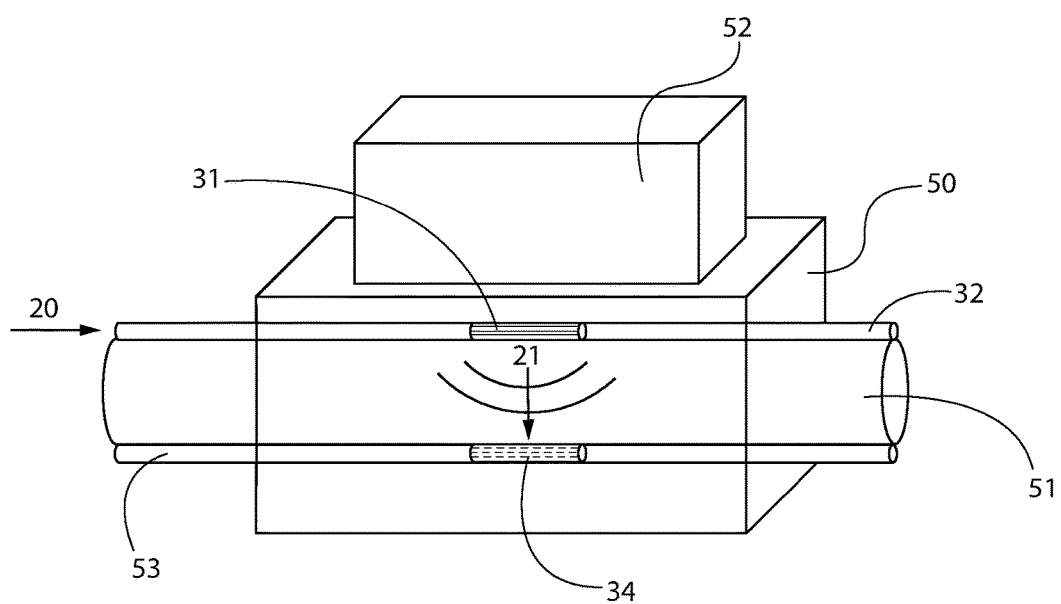
FIG. 6 is a schematic representation of the experimental set-up of Example 3.

The corrosion of a steel bar in a reinforced concrete slab was monitored using a photoacoustic generation element using the experimental configuration as illustrated in FIG. 6. FIG. 6 illustrates that a photoacoustic generation element 31 was positioned on a steel bar 51 embedded in a concrete slab 50. The photoacoustic generation element comprised gold nanocomposite that was prepared by blending a gold salt ($HAuCl_4 \cdot 3H_2O$) in polydimethylsiloxane. The photoacoustic generation element 31 with a length of 20 mm was coated on a sidewall of a multimode optical fiber 32 with a core having a diameter of 400 micrometer and a cladding having a diameter of 425 micrometer.

The optical fiber 32 was positioned on steel bar 51. The length of steel bar 51 was 300 mm and the diameter was 12.7 mm. A receiving optical fiber 53 comprising Bragg grating 34 was placed on the opposite side of the steel bar 51 using an epoxy resin. A 1,550 nm wavelength laser from a tunable laser (NewFocus TLB-6600, Newport) reflected from the Bragg grating 34 at strain free and the central wavelength was $\lambda_B$, the Bragg wavelength, and was determined by the grating period $\Lambda$, and the effective refractive index n, using the following equation $\lambda_B = 2\Lambda$. Both the photoacoustic generation element 31 and the Bragg grating 34 were centrally located on along the length of the steel bar as well as within the concrete slab.

The concrete slab was formed around the rebar by curing for 24 hours, submerging in water for 28 days, and air drying for 3 days. The concrete slab had a volume of 100 mm by 100 mm by 200 mm, using Type I/II ordinary Portland cement, sand, and gravel in the ratio of 1:2:3, and a water to cement ratio of 0.5.

A pulsed laser optical signal 20 having a wavelength of 532 nm emitted from a nanosecond laser (Surelite SL-10, Continuum) was directed through optical fiber 32. The energy from the optical signal 20 was converted into a thermal deformation in the photoacoustic generation element 31. Acoustic signal 21 was generated as a result of the thermal deformation and propagated on the surface of the rebar. The Bragg grating 34 detected the acoustic signal 21 by monitoring the change in strain of the ultrasound waves and the reflectivity of the Bragg grating spectra was transmitted to a photodetector (PDA10CS, Thorlabs), where the spectra shift of the Bragg wavelength was converted into a voltage signal. It was estimated that the velocity of the acoustic signal on the surface of the steel bar was 2,975.7 meters per second and that the time it took for the acoustic signal to reach the Bragg grating 34 was 6.9013 microseconds.

An acid solution 52 comprising 5 weight percent sodium chloride was placed on top of the concrete slab of Example 3 to accelerate the corrosion. After 7 days with the acid solution, a cathode was added to the acid solution 52 and an anode was attached to the steel bar to supply an electric charge of 10 V by means of a direct current. The acoustic signal was determined daily for 14 days under the electric charge. The concrete slab of Example 4 was not exposed to the accelerated corrosion conditions of the acid solution or the electric charge.

Figure 7:
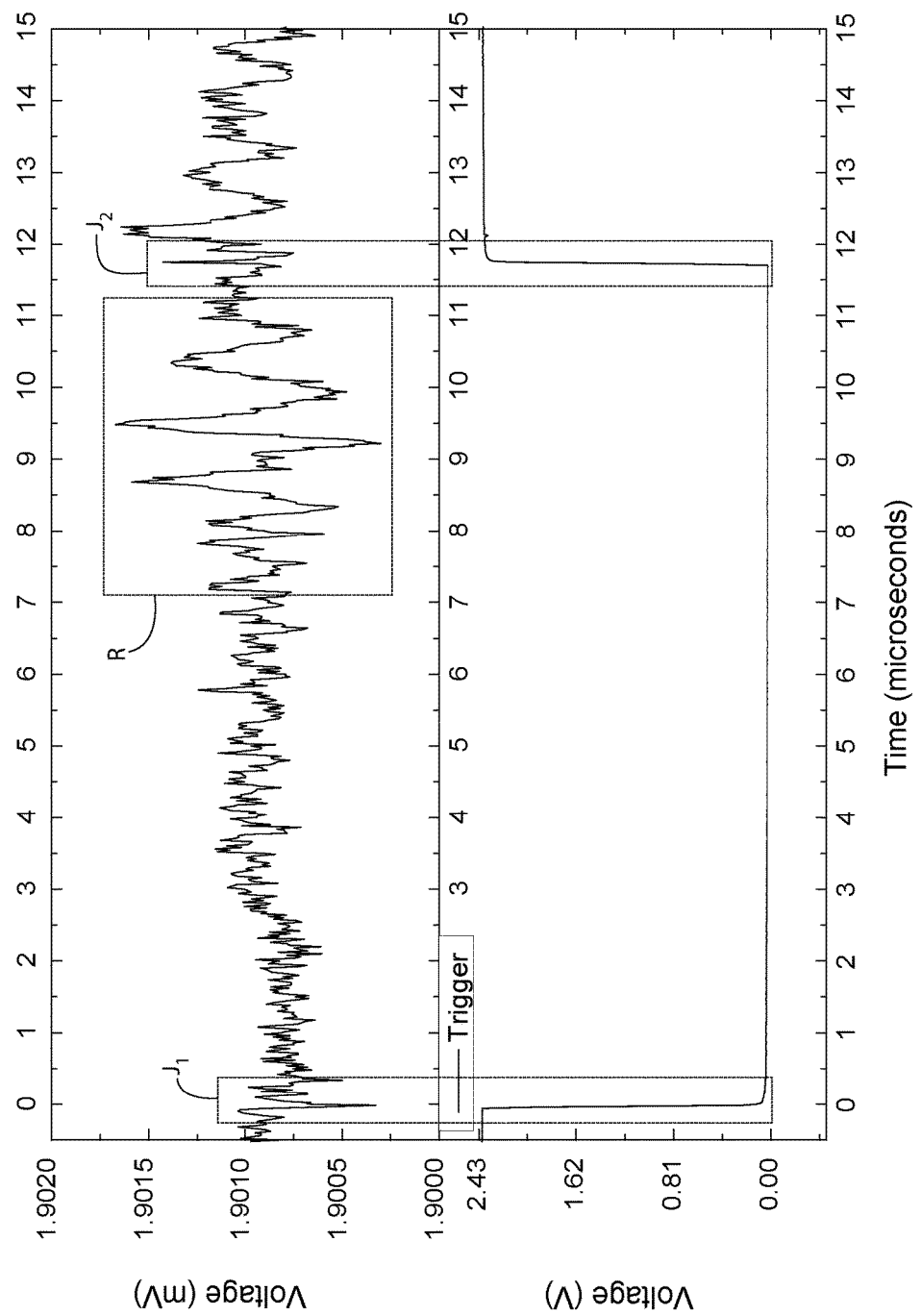
FIG. 7 is a graphical representation of an experimental signal of Example 3 before concreting in the time domain.

FIG. 7 is a graphical representation of an experimental signal of Example 3 before concreting in the time domain. Here, an optical signal was sent out from laser and the response was measured using a data acquisition card (M2i.4032, Spectrum). The start and end of a single optical signal, bottom graph, was defined as negative edge and positive edges of the voltage, V, respectively, and resulted in jumping waves, $J_1$ and $J_2$, respectively, in the measured voltage of the acoustic signal. The reflective signal, R, without corrosion was observed from 7 to 11 microseconds. The reflective laser signal was averaged for 99 times.

Figure 8:
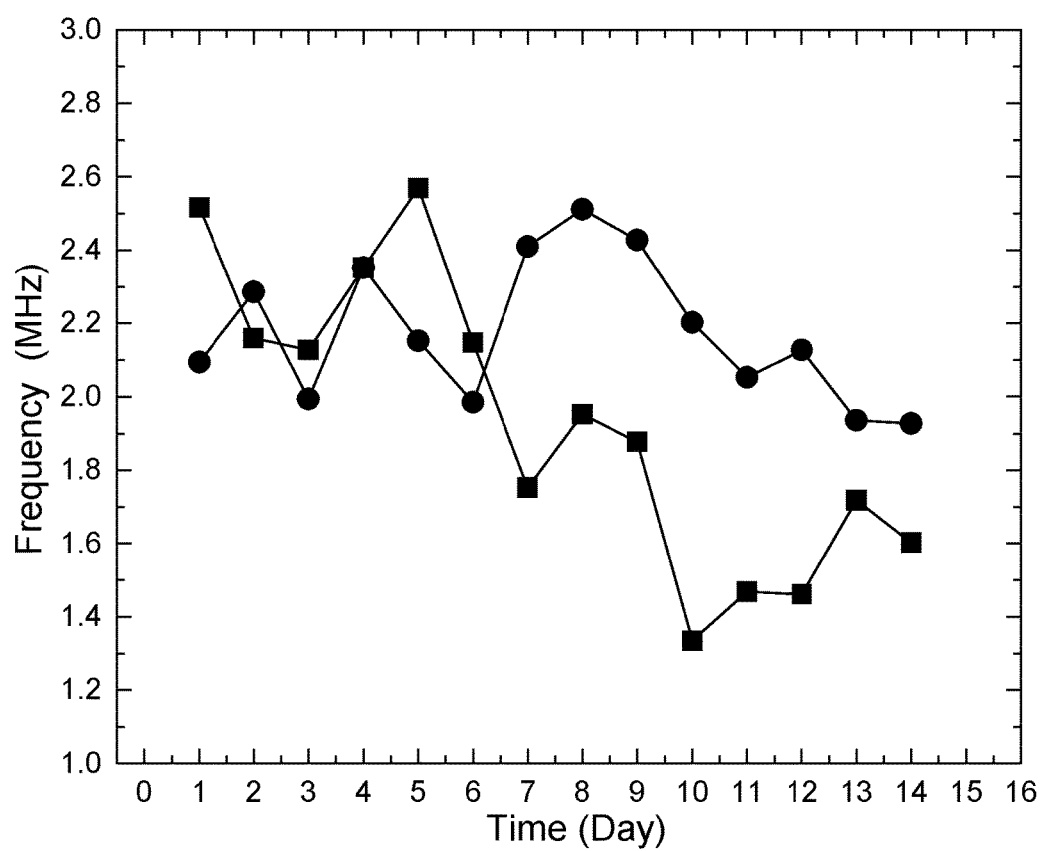
FIG. 8 is a graphical illustration of the mean values Examples 3 and 4.

The time domain data was converted using a Fast Fourier Transform and a bandpass filter from 8.3 to 8.7 megahertz. A central frequency of the acoustic signals was determined using the mean value of the Gaussian distribution of the Fast Fourier Transform data. FIG. 8 is a graphical illustration of the mean values Examples 3 and 4 versus time and are illustrated using the squares and circles, respectively. FIG. 8 illustrates that the central frequency for Example 3 begins to decrease around day 7. This decrease in the central frequency is a direct measure of the corrosion that is occurring on the surface of the rebar.

The corrosion of the steel bar of Examples 3 and 4 was then corroborated by removing the steel bars from the concrete slab. Visual corrosion was observed on the steel bar of Example 3. The steel bars were cleaned in accordance with ASTM G1-03 and the weight of the steel bars was determined. The mass loss for each bar was determined to be 0.33 and 0.11 weight percent, respectively, illustrating the increase in corrosion of the steel bar of Example 3 as compared to that of Example 4.

This example illustrates the ability of the present fiber sensor to determine the onset and occurrence of corrosion.

Set forth below are non-limiting embodiments of the present sensor.

Embodiment 1

A sensor comprising: a waveguide comprising a photoacoustic generation element disposed on the waveguide, the photoacoustic generation element comprising a photoabsorptive material; and an optical fiber comprising a sensing element comprising an optical acoustic wave detector.

Embodiment 2

A sensor comprising: a waveguide comprising a photoacoustic generation element disposed on the waveguide, the photoacoustic generation element comprising a photoabsorptive material, and a sensing element comprising an optical acoustic wave detector which is disposed in the waveguide.

Embodiment 3

A sensor comprising: a waveguide comprising a photoacoustic generation element disposed on the waveguide, the photoacoustic generation element comprising a photoabsorptive material and an optical switch; and an optical fiber comprising a sensing element comprising an optical acoustic wave detector.

Embodiment 4

A sensor comprising: a waveguide comprising a photoacoustic generation element disposed on the waveguide, the photoacoustic generation element comprising a photoabsorptive material and an optical switch; and a sensing element comprising an optical acoustic wave detector which is disposed in the waveguide.

Embodiment 5

The sensor of any of embodiments 1 to 4, wherein the waveguide is an optical fiber, and wherein the optical fiber of the waveguide is a same optical fiber as the optical fiber of the sensing element, or wherein the waveguide is a first optical fiber and the optical fiber of the sensing element is a second optical fiber.

Embodiment 6

The sensor of any of embodiments 1 to 5, wherein the optical fiber comprises an etched portion.

Embodiment 7

The sensor of any of embodiments 1 to 6, wherein the optical fiber comprises glass, a polymeric material, or combination thereof.

Embodiment 8

The sensor of any of embodiments 1 to 7, wherein the optical fiber is a single mode optical fiber having a core diameter of 1 µm to 9 µm.

Embodiment 9

The sensor of any of embodiments 1 to 8, comprising 1 to 3,000 photoacoustic generation elements.

Embodiment 10

The sensor of any of embodiments 1 to 9, comprising 1 to 3,000 sensing elements.

Embodiment 11

The sensor of any of embodiments 1 to 10, wherein the sensor comprises a plurality of photoacoustic generation elements, and wherein each photoacoustic generation element is disposed adjacent a corresponding sensing element.

Embodiment 12

The sensor of embodiment 11, wherein a distance between adjacent sensing elements is 0.01 meter to 1 meter.

Embodiment 13

The sensor of any of embodiments 11 to 12, wherein an average distance between adjacent sensing elements is 0.01 meter to 1 meter.

Embodiment 14

The sensor of any of embodiments 1 to 13, wherein the photoabsorptive material has a particle size of 10 nanometers to 500 nanometers.

Embodiment 15

The sensor of any of embodiments 1 to 14, wherein the photoabsorptive material has an average particle size of 10 nanometers to 500 nanometers.

Embodiment 16

The sensor of any of embodiments 1 to 15, wherein 90% of the photoabsorptive material has a particle size within 10% of the average particle size of the photoabsorptive material.

Embodiment 17

The sensor of any of embodiments 1 to 16, wherein 3 standard deviations of a particle size of the photoabsorptive material is 1 nanometer to 50 nanometers.

Embodiment 18

The sensor of any of embodiments 1 to 17, wherein the photoabsorptive material comprises gold, aluminum, silver, platinum, copper, carbon black, graphite, graphene, carbon nanotubes, a fullerene, or combination thereof.

Embodiment 19

The sensor of any of embodiments 1 to 18, wherein the photoabsorptive material comprises gold nanoparticles, gold nanorods, gold coated carbon nanotubes, gold coated fullerene, or combination thereof.

Embodiment 20

The sensor of any of embodiment 1 to 19, wherein the optical acoustic wave detector is a Bragg grating.

Embodiment 21

The sensor of any of embodiments 1 to 20, wherein the sensor is a temperature sensor, a corrosion sensor, or a material monitoring sensor for the detection of cracks or dislocations in a material.

Embodiment 22

A sensing system, the system comprising: the sensor of any of embodiments 1 to 21; and a laser.

Embodiment 23

The sensing system of embodiment 22, wherein the laser is capable of providing light having a wavelength of 1520 nm to 1560 nm.

Embodiment 24

The sensing system of any of embodiments 22 to 23, wherein the laser provides a pulse having a pulse width of 1 femtosecond to 1 microsecond.

Embodiment 25

The sensing system of any of embodiments 22 to 24, when the laser is capable of providing light having a wavelength which corresponds to an absorption wavelength of the photoabsorptive material.

Embodiment 26

The sensing system of any of embodiments 22 to 25, wherein the sensing system comprises a plurality of photoacoustic generation elements, and wherein the laser is configured to selectively provide light having a wavelength corresponding to an absorption wavelength of each photoacoustic generation element.

Embodiment 27

The sensing system of any of embodiments 22 to 26, wherein the sensing system is a temperature sensing system, a corrosion sensing system, or a material monitoring sensing system for the detection of cracks or dislocations in a material.

Embodiment 28

A method of temperature sensing, the method comprising: providing the sensing system of any of embodiments 22 to 27; heating the photoabsorptive material with a laser to generate an acoustic signal; sensing an intensity of laser light reflected by the optical acoustic wave detector to detect the acoustic signal; and determining a time of flight of the acoustic signal between the generation and the detection to determine a temperature of a medium between the photoabsorptive material and the optical acoustic wave detector.

Embodiment 29

The method of embodiment 28, wherein the medium is human tissue.

Embodiment 30

A method of corrosion sensing or material monitoring, the method comprising: providing the sensing system of any of embodiments 22 to 27; heating the photoabsorptive material with a laser to generate an acoustic signal; sensing an intensity of laser light reflected by the optical acoustic wave detector to detect the acoustic signal; and determining a time of flight of the acoustic signal between the generation and the detection to determine a parameter of a medium between the photoabsorptive material and the optical acoustic wave detector.

Embodiment 31

The method of any of embodiments 28 to 30, wherein the laser is directed into the waveguide.

Embodiment 32

The method of any of embodiments 28 to 31, wherein the waveguide is an optical fiber.

Embodiment 33

The method of any of embodiments 28 to 32, wherein the optical acoustic wave detector is a Bragg grating disposed in the optical fiber.

Embodiment 34

The method of any of embodiments 28 to 33, wherein a Bragg wavelength of the optical acoustic wave detector is shifted by acoustic pressure from the acoustic signal.

Embodiment 35

The method of any of embodiments 28 to 34, wherein the heating comprises selectively heating the photoabsorptive material of a selected photoacoustic generation element by contacting the photoabsorptive material of the selected photoacoustic generation element with laser light having a wavelength corresponding to an absorption wavelength of the photoabsorptive material of the selected photoacoustic generation element.

Embodiment 36

The method of any of embodiments 28 to 35, wherein the heating comprises selectively heating the photoabsorptive material of a selected photoacoustic generation element by selecting the selected photoacoustic generation element with the optical switch.

Embodiment 37

The method of any of embodiments 28 to 36, wherein the method is a method of temperature sensing, the method of corrosion sensing, or a method of material monitoring for the detection of cracks or dislocations in a material.

Embodiment 38

The method of any of embodiments 29 to 37, wherein the sensor comprises a plurality of sensing elements, and further comprising developing a temperature distribution profile based on the temperature and location of each sensing element.

The terms "a" and "an" do not denote a limitation of quantity, but rather denote the presence of at least one of the referenced item. The term "or" means "and/or" unless clearly indicated otherwise by context. Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments. "About" is intended to include the degree of error associated with measurement of the particular quantity based upon the equipment available at the time of filing the application. The terms "first," "second," and the like, "primary," "secondary," and the like, as used herein do not denote any order, quantity, or importance, but rather are used to distinguish one element from another. The term "combination" is inclusive of blends, mixtures, alloys, reaction products, and the like. Unless defined otherwise, technical and scientific terms used herein have the same meaning as is commonly understood by one of skill in the art to which this disclosure belongs.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

Unless specified to the contrary herein, all test standards are the most recent standard in effect as of the filing date of this application, or, if priority is claimed, the filing date of the earliest priority application in which the test standard appears.

The endpoints of all ranges directed to the same component or property are inclusive of the endpoints, are independently combinable, and include all intermediate points and ranges (e.g., ranges of "up to 25 wt %, or more specifically 5 to 20 wt %" is inclusive of the endpoints and all intermediate values of the ranges of "5 to 25 wt %," such as 10 to 23 wt %, etc.).

All cited patents, patent applications, and other references are incorporated herein by reference in their entirety. However, if a term in the present application contradicts or conflicts with a term in the incorporated reference, the term from the present application takes precedence over the conflicting term from the incorporated reference.

What is claimed is:

1. A sensor comprising:
  a waveguide comprising a photoacoustic generation element disposed on a side wall of the waveguide, the photoacoustic generation element comprising a photoabsorptive material, wherein the photoabsorptive material has an average particle size of 10 nanometers to 500 nanometers and, wherein 90% of the photoabsorptive material has a particle size within 10% of the average particle size of the photoabsorptive material; and
  a sensing element comprising an optical acoustic wave detector.

2. The sensor of claim 1, wherein the waveguide comprises both the photoacoustic generation element and the sensing element; wherein the sensing element is disposed in the waveguide.

3. The sensor of claim 1, wherein the waveguide is a first optical fiber and a second optical fiber comprises the sensing element.

4. The sensor of claim 1, further comprising an optical switch.

5. The sensor of claim 1, comprising one or both of 1 to 3,000 photoacoustic generation elements and 1 to 3,000 sensing elements.

6. The sensor of claim 1, wherein the sensor comprises a plurality of photoacoustic generation elements, and wherein each photoacoustic generation element is disposed adjacent a corresponding sensing element.

7. The sensor of claim 1, wherein the photoabsorptive material comprises gold, aluminum, silver, platinum, copper, carbon black, graphite, graphene, carbon nanotubes, a fullerene, or combination thereof.

8. The sensor of claim 1, wherein the optical acoustic wave detector is a Bragg grating.

9. The sensor of claim 1, wherein the sensor is a temperature sensor, a corrosion sensor, or a material monitoring sensor for the detection of cracks or dislocations in a material.

10. A sensing system, the system comprising:
the sensor of claim 1; and a laser.

11. The sensing system of claim 10, wherein the laser is configured to provide light having a wavelength of 1,520 nm to 1,560 nm.

12. The sensing system of claim 10, wherein the laser is configured to provide light having a wavelength which corresponds to an absorption wavelength of the photoabsorptive material.

13. The sensing system of claim 10, wherein the sensing system comprises a plurality of photoacoustic generation elements, and wherein the laser is configured to selectively provide light having a wavelength corresponding to an absorption wavelength of each photoacoustic generation element.

14. A method of sensing, the method comprising:
providing the sensing system comprising a sensor and a laser; wherein the sensor comprises a waveguide and a sensing element comprising an optical acoustic wave detector, the waveguide comprising a photoacoustic generation element disposed on a side wall of the waveguide, and the photoacoustic generation element comprising a photoabsorptive material;
heating the photoabsorptive material with the laser to generate an acoustic signal;
sensing an intensity of laser light reflected by the optical acoustic wave detector to detect the acoustic signal; and
determining a time of flight of the acoustic signal between the generation and the detection to determine a change in a parameter change in a medium between the photoabsorptive material and the optical acoustic wave detector.

15. The method of claim 14, wherein the method of sensing comprises detecting a change in temperature, a material crack, a material dislocation, or a change in corrosion.

16. The method of claim 14, wherein the method of sensing comprises detecting a change in temperature; wherein one or both of (a) the medium is human tissue and (b) the sensor comprises a plurality of sensing elements and the method comprises developing a temperature distribution profile based on the temperature and location of each sensing element.

17. The method of claim 14, wherein the method of sensing comprises detecting a change in corrosion and wherein the medium is optionally a steel reinforced concrete.

18. The method of claim 14, wherein a Bragg wavelength of the optical acoustic wave detector is shifted by acoustic pressure from the acoustic signal.

19. The method of claim 14, wherein the heating comprises selectively heating the photoabsorptive material of a selected photoacoustic generation element by selecting the selected photoacoustic generation element with the optical switch.

20. The method of claim 14, wherein the photoabsorptive material has an average particle size of 10 nanometers to 500 nanometers and, wherein 90% of the photoabsorptive material has a particle size within 10% of the average particle size of the photoabsorptive material.

* * * * *